United States Patent [19]
Adams et al.

[11] Patent Number: 5,264,457
[45] Date of Patent: Nov. 23, 1993

[54] PHENYL AMIDINES SULFONAMIDES USEFUL AS PLATELET AGGREGATION INHIBITORS

[75] Inventors: Steven P. Adams, St. Charles; Joseph G. Rico, Manchester, both of Mo.; Masateru Miyano, Northbrook, Ill.

[73] Assignee: G. D. Searle & Co., Chicago, Ill.

[21] Appl. No.: 837,310

[22] Filed: Feb. 14, 1992

[51] Int. Cl.$^5$ .................. A61K 31/24; A61K 31/195; C07C 317/06; C07C 317/14
[52] U.S. Cl. .................. 514/539; 514/538; 514/562; 560/13; 562/430
[58] Field of Search .......... 560/13; 562/430; 514/538, 539, 562

[56] References Cited

U.S. PATENT DOCUMENTS

| | | | |
|---|---|---|---|
| 4,578,079 | 3/1986 | Ruoslahti et al. | 623/11 |
| 4,791,102 | 12/1988 | Bernat et al. | 514/19 |
| 4,857,508 | 8/1989 | Adams et al. | 514/18 |
| 4,879,313 | 11/1989 | Tjoeng et al. | 514/616 |
| 4,977,168 | 12/1990 | Bernat et al. | 514/330 |

FOREIGN PATENT DOCUMENTS 0275748 7/1988 European Pat. Off. .
0298820 1/1989 European Pat. Off. .

OTHER PUBLICATIONS

Ruggeri, et al., *Proc. Natl. Acad. Sci.*, 83, pp. 5708–5712, (1986).
Ginsberg, et al., *J. Biol. Chem.*, 260, (7), pp. 3931–3936, (1985).
Wagner, et al. *Chemical Abstracts*, 100:25, p. 652, Abstract No. 210409z, Jun. 18, 1984.
Vieweg, et al. *Chemical Abstracts*, 108:25, p. 613, Abstract No. 222085u, Jun. 20, 1988.
Stuerzebecher et al., *Chemical Abstracts*, 111:9, pp. 245–252, Abstract No. 70318u, Aug. 28, 1989.

*Primary Examiner*—José G. Dees
*Assistant Examiner*—Vera C. Clarke
*Attorney, Agent, or Firm*—Joy Ann Serauskas; Roger A. Williams

[57] ABSTRACT

This invention relates to compounds having the following formula

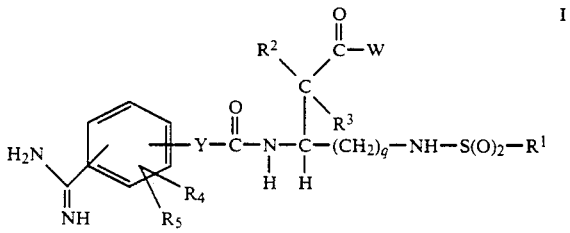

which are useful in the inhibition of platelet aggregation. This invention also relates to pharmaceutical compositions of such phenyl amidine sulfones derivatives.

19 Claims, No Drawings

PHENYL AMIDINES SULFONAMIDES USEFUL AS PLATELET AGGREGATION INHIBITORS

FIELD OF THE INVENTION

This invention is in the field of mammalian therapeutics and relates to compounds for the treatment of mammalian disorders such as cardiovascular disorders. Of particular interest is a class of phenyl amidines derivatives useful as inhibitors of platelet aggregation.

BACKGROUND OF THE INVENTION

Fibrinogen is a glycoprotein present as a normal component of blood plasma. It participates in platelet aggregation and fibrin formation in the blood clotting mechanism.

Platelets are cellular elements found in whole blood which also participate in blood coagulation. Fibrinogen binding to platelets is important to normal platelet function in the blood coagulation mechanism. When a blood vessel receives an injury, the platelets binding to fibrinogen will initiate aggregation and form a thrombus. Interaction of fibrinogen with platelets occurs through a membrane glycoprotein complex, known as gp IIb-/IIIa; this is an important feature of the platelet function. Inhibitors of this interaction are useful in modulating platelet thrombus formation.

It is also known that another large glycoprotein named fibronectin, which is a major extracellular matrix protein, interacts with fibrinogen and fibrin, and with other structural molecules such as actin, collagen and proteoglycans. Various relatively large polypeptide fragments in the cell-binding domain of fibronectin have been found to have cell-attachment activity. See U.S. Pat. Nos. 4,517,686; 4,589,881; and 4,661,111. Certain relatively short peptide fragments from the same molecule were found to promote cell attachment to a substrate when immobilized on the substrate or to inhibit attachment when in a solubilized or suspended form. See U.S. Pat. Nos. 4,578,079 and 4,614,517.

In U.S. Pat. No. 4,683,291, inhibition of platelet function is disclosed with synthetic peptides designed to be high affinity antagonists of fibrinogen binding to platelets. U.S. Pat. No. 4,857,508 discloses tetrapeptides having utility as inhibitors of platelet aggregation.

Other synthetic peptides and their use as inhibitors of fibrinogen binding to platelets are disclosed by Koczewiak et al., Biochem. 23, 1767-1774 (1984); Plow et al., Proc. Natl. Acad. Sci. 82, 8057-8061 (1985); Ruggeri et al., Ibid. 83, 5708-5712 (1986); Ginsberg et al., J. Biol. Chem. 260 (7), 3931-3936 (1985); Haverstick et al., Blood 66 (4), 946-952 (1985); and Ruoslahti and Pierschbacher, Science 238, 491–497 (1987). Still other such inhibitory peptides are disclosed in EP Patent Applications 275,748 and 298,820.

U.S. Pat. No. 4,879,313 discloses compounds useful as inhibitors of platelet aggregation having the formula:

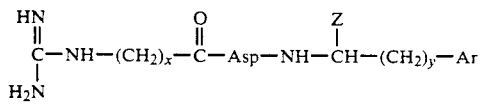

wherein
x = 6 to 10,
y = 0 to 4,
Z = H, COOH, CONH$_2$ OR C$_{1-6}$ alkyl,

Ar = phenyl, biphenyl or naphthyl, each substituted with 1 to 3 methoxy groups, or an unsubstituted phenyl, biphenyl, naphthyl, pyridyl or thienyl group, and Asp = aspartic acid residue.

These compounds lack the phenyl amidine moiety and the sulfonyl moiety of the present invention.

U.S. Pat. No. 4,977,168 discloses compounds having the following structural formula:

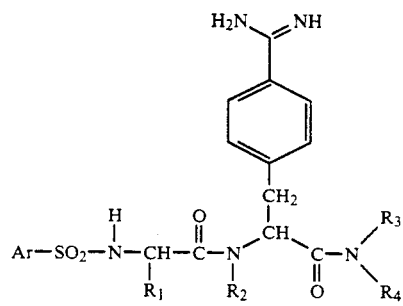

wherein

R$_1$ represents hydrogen, a lower alkyl group, a lower hydroxyalkyl group, a benzyl group, a phenyl group or a 4-hydroxyphenyl group;

R$_2$ represents a lower alkyl, lower alkenyl, lower alkynyl or benzyl group, or a lower alkoxycarbonylalkyl, lower carboxyalkyl, or lower hydroxyalkyl group;

R$_3$ and R$_4$, identical or different, each represents a lower alkyl or lower hydroxyalkyl radical, lower alkenyl or lower alkynyl radical or form together with the nitrogen to which they are attached, a saturated heterocycle such as morpholino, thiomorpholino, pyrrolidino not substituted or substituted by an alkoxycarbonyl or carboxy group, piperazino, 4-(lower alkyl)piperazino, 4-(lower hydroxyalkyl)piperazino, or piperidino not substituted or substituted by one of the following groups: lower alkyl, benzyl, hydroxy, lower hydroxyalkyl, amino, lower aminoalkyl, hydroxyamino, alkoxycarbonyl or carboxy.

Ar represents a phenyl, alpha-naphthyl or beta-naphthyl group, possibly substituted, or a heteroaryl group chosen from the radicals pyridyl, quinolinyl, or isoquinolinyl, possibly substituted, as well as their isomers and their mixtures and their salts with pharmaceutically acceptable mineral or organic acids which are useful as antithrombotic agents. These compounds are structurally distinct from the present invention because they are amidinophenylalaninamides.

U.S. Pat. No. 4,791,102 discloses compounds having the following structural formula

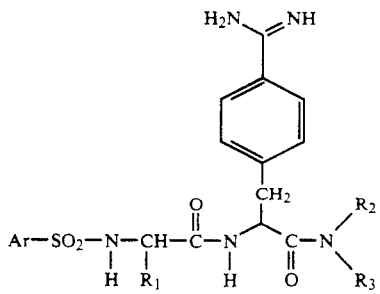

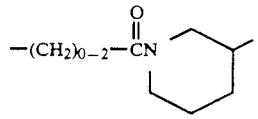

wherein
R₁ represents a lower alkyl, lower hydroxyalkyl, or benzyl group, a phenyl or a 4-hydroxyphenyl group.

R₂ and R₃, identical or different, each represents a lower alkyl or hydroxyalkyl, lower alkenyl or lower alkynyl radical, or they form together with the nitrogen to which they are attached, a saturated heterocycle such as morpholino, thiomorpholino, pyrrolidino unsubstituted or substituted by an alkoxycarbonyl or carboxyl group, piperazino, 4-(lower alkyl)-piperazino or piperidino unsubstituted or substituted by a lower alkyl, benzyl, hydroxy, lower hydroxyalkyl, amino, lower aminoalkyl, alkoxycarbonyl or carboxyl group.

Ar represents a phenyl, a possibly substituted alpha-naphthyl or beta-naphthyl group, or else a heteroaryl group chosen from pyridyl, quinolinyl, isoquinolinyl, possibly substituted which are useful as selective inhibiting agents of thrombin and antithrombotics. These compounds are structurally distinct from the present invention because they are amidinophenylalaninamides.

European Patent Application 372,486 discloses N-acyl beta amino acid derivatives of the formula:

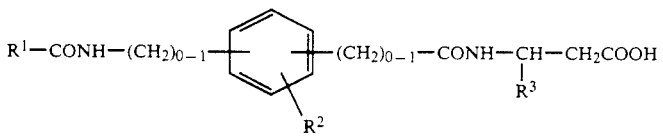

and their salts. Said compounds are useful for inhibiting platelet aggregation in the treatment of thrombosis, stroke, myocardial infarction, inflammation and arteriosclerosis, and for inhibiting metastasis.

European Patent Application 381,033 A1 discloses amidino or guanidino-aryl substituted alkanoic acid derivatives which are useful for the treatment of thrombosis, apoplexy, cardiac infarction, inflammation, arteriosclerosis and tumors. These compounds are structurally distinct from the present invention because they lack the sulfonyl moiety of the present invention.

European Patent Application 445,796 A2 discloses acetic acid derivatives having the formula

H₂N(NH)C—X—Y—CO—Z—CH(Q¹)COOQ² where
Q¹ stands for hydrogen, methyl or phenyl,
Q² stands for hydrogen, phenyl-low-alkyl or low alkyl that can be cleaved under physiological conditions, X stands for 1,4-phenylene, 2,5- or 3,6-pyridylene or, 1,4-piperidinylene, which is bonded to group Y through the C atom in the 4-position,
Y is a group having the formula $$-(CH_2)_{0-2}-CONHCH(Q^3)(CH_2)_{1-3} \quad (Y^1)$$

$$-CONHCH_3CH(Q^4) \quad (Y^2)$$

$$-(CH_2)_3NHCOCH_2- \quad (Y^3)$$

$$-NHCO(CH_2)_3- \quad (Y^4)$$

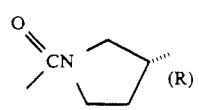

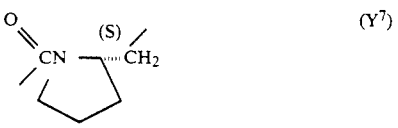

where
Q³ stands for hydrogen, methyl, phenyl, —COOH, —COO-low-alkyl, —CONH(CH₂)₂—COOH or —CONH(CH₂)₂—COO-low-alkyl,
Q⁴ hydrogen, methyl or phenyl,
Z a 1,4-piperazinylene group, a 1,4-piperazinylene group which is bonded to the CO group through the N atom in the 1-position or a group having the formula —NHCH(R¹)—or—NHCH(COR²)— where
R¹ stands for hydrogen, methyl, phenyl or a —COO-low-alkyl,
R² stands for the residue of an α-aminocarboxylic acid bonded through the amino group or of an ester or amide thereof, or a group having the formula —NHCH₂CH₂—Ar, or —CO—R², or, if applicable, a mono-or di-low-alkylated carbamoyl group or a pyrrolidinoyl or piperidinoyl group,
Ar stands for a phenyl or a phenyl substituted by low alkyl, low alkoxy, —COOH, —COO-low-alkyl, —O(CH₂)₁₋₄—COOH, —O(CH₂)₁₋₄—COO-low-alkyl, —CONH₂, —CONH-low-alkyl, —CON(-low alkyl)₂, pyrrolidinoyl or piperidinoyl which are said to have inhibitory action on the bonding of adhesive proteins to blood platelets as well as blood platelet aggregation and cell-cell adhesion. These compounds are structurally distinct from the present invention because the lack the sulfonyl moiety of the present invention.

SUMMARY OF THE INVENTION

The present invention relates to a class of compounds represented by the formula:

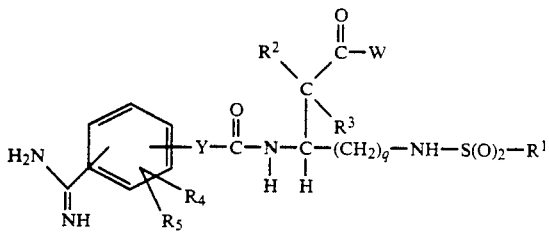

or a pharmaceutically acceptable salt thereof, wherein
R¹ is hydrogen, alkyl having 1 to 6 carbon atoms, phenyl or substituted phenyl wherein each substituent is selected from the group consisting of alkyl having 1 to 6 carbon atoms, halo, alkoxy having 1 to 6 carbon atoms, trifluoromethyl and hydroxy;
R² and R³ are each independently hydrogen or alkyl having 1 to 6 carbon atoms;
R⁴ and R⁵ are each independently hydrogen, alkyl having 1 to 6 carbon atoms, alkoxy having 1 to 6 carbon atoms or halo;
W is the radical OR wherein R is hydrogen or alkyl having 1 to 6 carbon atoms;
Y is alkyl having 1 to 6 carbon atoms, alkenyl having 2 to 4 carbon atoms or alkynyl having 2 to 4 carbon atoms; and
q is an integer from 1 to 3.

The invention further relates to pharmaceutical compositions comprising a compound of Formula I. Such compounds and compositions have usefulness as inhibitors of platelet aggregation. The invention also relates to a method of inhibiting platelet aggregation in a mammal in need of such treatment.

A preferred embodiment of the present invention is a compound of the formula

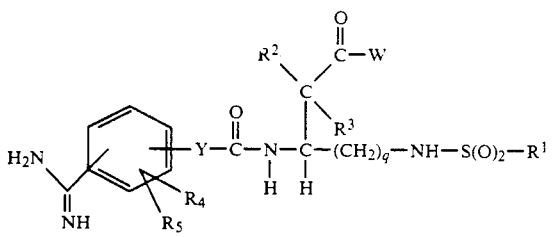

or a pharmaceutically acceptable salt thereof, wherein
R¹ is hydrogen, phenyl or substituted phenyl wherein each substituent is selected from the group consisting of alkyl having 1 to 6 carbon atoms, halo, alkoxy having 1 to 6 carbon atoms, trifluoromethyl and hydroxy;
R² and R³ are each independently hydrogen;
R⁴ and R⁵ are each independently hydrogen,
W is the radical OR wherein R is hydrogen or alkyl having 1 to 6 carbon atoms;
Y is alkyl having 1 to 6 carbon atoms; and
q is an integer from 1 to 3.

Exemplifying this embodiment are the following compounds:

(±)-ethyl 3-[[5-[4-(aminoiminomethyl)phenyl]-1-oxopentyl]amino]-4-[[(4-methylphenyl)sulfonyl]amino]butanoate;

(±)-3-[[5-[4-(aminoiminomethyl)phenyl]-1-oxopentyl]amino]-4-[[(4-methylphenyl)sulfonyl]amino]-butanoic acid; and (±)-3-[[5-[4-(aminoiminomethyl)phenyl]-1-oxopentyl]amino]-4-[[(4-methoxyphenyl)sulfonyl]amino]-butanoic acid.

As used herein, the term "hydrido" denotes a single hydrogen atom (H). This hydrido group may be attached, for example, to a oxygen atom to form a hydroxyl group; or, as another example, two hydrido groups may be attached to a carbon atom to form a —CH₂-group.

As used herein, the term "alkyl" embraces a linear or branched chain saturated hydrocarbon radical having 1 to 6 carbon atoms. Illustrative of such radicals are methyl, ethyl, propyl, 1-methylethyl, butyl, 2-methylpropyl, 1-methylpropyl, 1,1-dimethylethyl, pentyl, 3-methylbutyl, 1-methylbutyl, 1-ethylpropyl, 2,2-dimethylpropyl, 1,1-dimethylpropyl, hexyl, and 4-methylpentyl.

As used herein, the term "alkoxy" embraces linear or branched oxy-containing radicals each having alkyl portions of 1 to 6 carbon atoms. Illustrative of such groups are methoxy, ethoxy, propoxy, butoxy, 1-methylethoxy, 2-methylpropoxy, 1-methylpropoxy, 1,1-dimethylethoxy, pentenoxy, 3-methylbutoxy, 1-methylbutoxy, 1-ethylpropoxy, 2-2-dimethylpropoxy, 1,1-dimethylpropoxy, hexoxy, and 4-methylpentoxy.

As used herein the term "alkenyl" embraces linear or branched unsaturated hydrocarbon radicals having 2 to 6 carbon atoms and containing at least one carbon to carbon double bond, which carbon to carbon double bond may have either cis or trans geometry within the alkenyl moiety. Illustrative of such groups are ethenyl, propenyl, butenyl, isobutenyl, pentenyl, 3-methyl-1-butenyl, 2-methyl-2-butenyl, 2,3-dimethyl-2-butenyl, and hexenyl.

As used herein the term "alkynyl" embraces linear or branched unsaturated hydrocarbon radicals having 2 to 6 carbon atoms and containing one carbon to carbon triple bond. Illustrative of such radicals are ethynyl, propynyl, butynyl, isobutynyl, pentynyl, 2-methyl-2-butynyl, and hexynyl.

As used herein the term "halo" embraces halogen atoms. Illustrative of such atoms are chloro (Cl), fluoro (F), bromo (Br) and iodo (I).

The compounds as shown in Formula I can exist in various isomeric forms and all such isomeric forms are meant to be included. Tautomeric forms are also included as well as pharmaceutically acceptable salts of such isomers and tautomers.

In the structures and formulas herein, the bond drawn across a bond of an aromatic ring can be to any available atom on the aromatic ring.

The term "pharmaceutically acceptable salt" refers to a salt prepared by contacting a compound of formula (I) with an acid whose anion is generally considered suitable for human consumption. Examples of pharmacologically acceptable salts include the hydrochloride, hydrobromide, hydroiodide, sulfate, phosphate, acetate, propionate, lactate, maleate, malate, succinate, and tartrate salts. All of these salts may be prepared by conventional means by reacting, for example, the appropriate acid with the corresponding compound of Formula I.

DETAILED DESCRIPTION OF THE INVENTION

The compounds of Formula I may be prepared by standard synthetic methods combined with methods analogous to solution phase peptide synthesis [see: The Peptides: Analysis, Synthesis, Biology (E. Gross and J. Meienhofer, eds.), Vol. 1-5, Academic Press, New York)].

General synthetic sequences are outlined in the following Schemes.

In Scheme 1 is described a general synthesis of the 5-(cyanophenyl)-pentanoic, -pentenoic and -pentynoic derivatives, substituted or not. A halobenzonitrile is coupled to an omega alkenoic or alkynoic acid using a palladium based coupling reaction ["Heck Reaction"- *Palladium Reagents in Organic Syntheses* (Richard F. Heck), Academic Press, New York, 1985; Heck, R. F. *J. Amer. Chem. Soc.*, 1979, 12, 146-51. Tuyet, J. *J. Chem. Soc., Chem. Commun.* 1984, 1287-9]. The preferred conditions for the palladium coupling reaction generally differ for the alkynoic acid and the alkenoic acid coupling components. The preferred conditions for the alkynoic acid coupling component utilizes tetrakis(triphenylphosphine)-palladium as catalyst and piperidine as the solvent (for related conditions see: H. A. Dieck and F. R. Heck *J. Organometallic Chem.* 259-263 (1975)). Suitable conditions for the alkenoic acid coupling component utilize the phase transfer conditions of Jeffery and Larock [T. Jeffery *J. Chem. Soc. Chem. Commun.* 1287-89 (1984); R. C. Larock *Tetrahedron Lett.* 2603-2606 (1989)]. These extremely mild conditions (phase transfer agent-tetrabutylammonium salt, catalyst palladium (II) acetate, base-potassium acetate or triethylamine, dimethyl formamide) afford a good yield of coupled olefin. Compounds of Formula I where Y is a saturated chain (alkane) are obtained through a selective reduction of the double bond (Y is CH=CH) by catalytic reduction over palladium on calcium carbonate. The required omega alkenoic acids are commercially available or can be synthesized by oxidation of the omega alkenols [E. J. Corey and G. Schmidt *Tetrahedron Lett.* 399 (1979)]. The required omega alkynoic acids are commercially available or can be synthesized from omega haloalkanoic acids and lithium acetylide [W. J. DeJarlais, E. A. Emken *Synth. Commun.* 653 (1980); J. Cossy, J. P. Pete *Tetrahedron Lett.* 573 (1986)].

In Scheme 2 is described an alternative method for the preparation of the (cyanophenyl)alkenoic acid unit using a standard Wittig Reaction [B. E. Maryanoff, A. Reitz *Chem Rev.* 863-927 (1989)] with cyanobenzaldehyde and an omega substituted (carboxyalkyl)triphenylphosphonium bromide as the two reaction components [for related conditions see: *J. Am. Chem. Soc.*, 397 (1970); Ibid 6831 and 7185 (1973)].

In Scheme 3 are included examples of procedures to access compounds of Formula I where $R_1$ and $R_2$ are different from hydrogen. The substituents $R_1$ and $R_2$, (where $R_1$ and $R_2$ are each independently halo, alkyl, hydroxy, or alkoxy) can be present in the starting commercially available bromobenzonitrile (Scheme 1) cyanobenzaldehyde (Scheme 2) or introduced at a latter stage as indicated in Scheme 3. The ring can be halogenated using bromine, iodine, or chlorine (Scheme 3). Introduction of fluorine on the ring is best performed at the expense of the corresponding amino derivative, using diazotization followed by dediazonation in the presence of fluoride-containing counterion (D. E. Rosenberg and al., *Tet. Let.*, 21, 4141-4, 1980; Scheme 3a). Other modifications of this method can also be useful (Rosenfeld and Widdowson, JCS Chem. Comm. 914, 1979). An alkyl group can be introduced by low temperature lithium halogen exchange followed by quenching with the appropriate aldehyde [see: W. E. Parham, C. K. Bradsher *Acct. Chem. Res.* 300 (1982)]. The resultant alcohol can be converted to an alkyl by hydrogenolysis [*Reductions in Organic Chemistry* (M. Hudlicky, ed.), John Wiley & Sons, New York, 1984] as shown in Scheme 3. The substituents, wherein $R_1$ and $R_2$ are each independently hydroxy or alkoxy, can be introduced by low temperature lithium halogen exchange followed by quenching with the electrophilic bis(trimethylsilyl) peroxide [(TMSO)$_2$-Scheme 3) M. Taddei and A. Ricci *Synthesis* 633-635 (1986)] which affords the silyl ether. The silyl ether can be converted to OH by treatment With hydrochloric acid [M. Taddei and A. Ricci ibid]. The alkoxy group (OR wherein R is alkyl having 1 to 6 carbon atoms) can be introduced by treating the derivative OH with weak base (K$_2$CO$_3$) and an appropriate alkyl halide [2 equivalents, see: C. F. H. Allen and J. W. Gates, Jr. *Organic Syntheses* Coll. Vol 3 140 (1955)] which will, in addition, form the ester. The ester can be selectively cleaved in the presence of the ether with one equivalent of sodium hydroxide (Scheme 3). The derivative where Y is carbonyl can be introduced at the benzonitrile stage using the synthetic Scheme 4a. Scheme 4b describe the conversion of the cyano group into the amidine group via the thioimidate. The thioimidate is formed by first treating the cyano compound with hydrogen sulfide (H$_2$S) followed by alkylation with methyl iodide. Next, treatment of the thioimidate with ammonium acetate affords the amidine as the salt (HI). Alternatively (Scheme 4c) the nitrile can be converted to the amidine by the use of lithium bis(trimethylsilyl)amide in an inert solvent such as diethyl ether (R. T. Boere et al, *J. Organomet. Chem.*, 331, 161-67, 1987).

Scheme 5 describes the synthesis of the sulfonamide 4-(tolylsulfamido)-3-amino ethyl butyrate from amino acetaldehyde dimethyl acetal. First, the tolylsulfonamide moiety is attached using p-toluenesulfonyl chloride in methylene chloride and triethylamine. The acetal is then removed with aqueous HCl and water soluble solvent such as acetonitrile, tetrahydrofuran, dimethoxy ethane or dioxane. The aldehyde can be obtained by reaction with ethyl diazoacetate in the presence of zinc chloride (E. J. Roskamp et al., *J Org. Chem.* 3258-3260, 54, 1989). The β-keto ester is obtained by reductive amination using excess ammonium formate and sodium cyanoborohydride in methanol. The 4-(toluensulfonamido)-3-amino acid is obtained by hydrolysis with sodium hydroxide followed by acidification and purification by reverse phase chromatography.

Scheme 6 outlines an alternate general route for preparation of 4-(sulfonamido)-3-amino acids. The ethyl 4-amino-3-hydroxybutyrate is obtained from the acid using HCl in ethanol/dioxane which is then reacted with methoxybenzene sulfonyl chloride and triethylamine in dichloromethane to afford sulfonamide. The 3-hydroxyl group is converted to amine either by mesylation, displacement with azide and reduction, or by oxidation with pyridinium chlorochromate in an aprotic solvent such as dichloromethane followed by reductive amination as described previously.

Alternatively, optically active 4-(arylsulfonamido)-3-aminobutyrates can be prepared from optically active aspartame (Scheme 7). The appropriately protected N-tBOC-L-aspartate-β-benzyl ester is converted to the key optically active alcohol using borane-THF [C. Stanfield et al., *J. Org. Chem.*, 6, 4797-4798 (1981)] and then one of two routes to product may be employed. The alcohol can be converted to the aldehyde, reductively aminated and then reacted with an appropriate sulfonyl chloride. Alternatively, the alcohol can be converted to the mesylate, displaced with sodium azide in DMF or appropriate polar solvent reduced to the amine by catalytic reduction or by reaction with triphenylphosphine, followed utliamtely by reaction with sulfonyl chloride and triethylamine in an aprotic solvent.

Compounds of Formula I can be obtained by coupling any one of the acid derivatives obtained in Schemes 1-4 with any of the amines obtained as described in Schemes 5-7. As outlined in Scheme 8, coupling is effected with an activated form of the acid which may include anhydride, acid chloride or any of a variety of active esters as described in *Principles of Peptide Synthesis*, Bodansky, 1984, Springer-Verlag. Preferentially, the amide bonds are formed using standard coupling reagents, e.g. dicyclohexylcarbodiimide (DCC), carbonyldiimidazole, disuccinimidyl carbonate (DSC), benzotriazole-1-yl-oxy-tris-(dimethylamino)-phosphonium hexafluorophosphate (BOP) or isobutyl chloroformate (mixed anhydride method).

Purification of final compounds is usually by reverse phase high pressure liquid chromatography [*High Performance Liquid Chromatography Protein and Peptide Chemistry*, F. Lottspeich, A. Henscher, K. P. Hupe, eds.) Walter DeGruyter, New York, 1981) or crystallization.

SCHEME 1

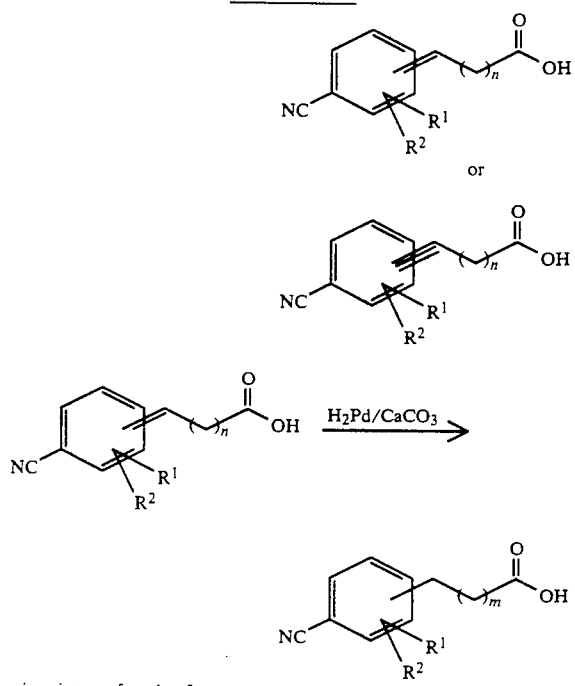

n is an interger from 1 to 3
m is an interger from 0 to 5

SCHEME 2

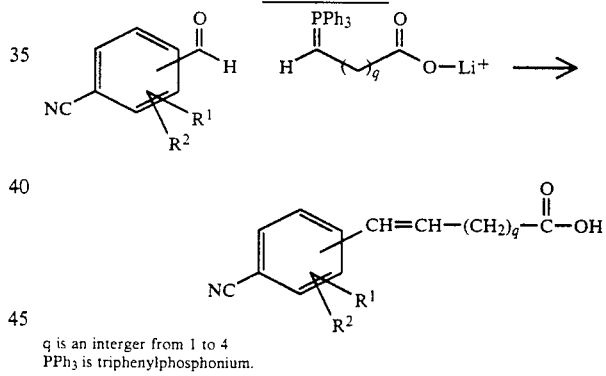

q is an interger from 1 to 4
PPh₃ is triphenylphosphonium.

SCHEME 3

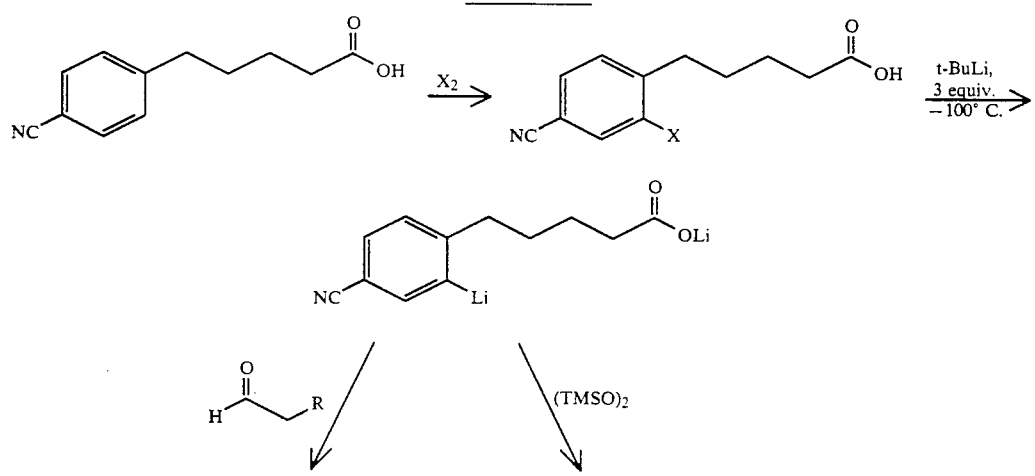

5,264,457
SCHEME 3
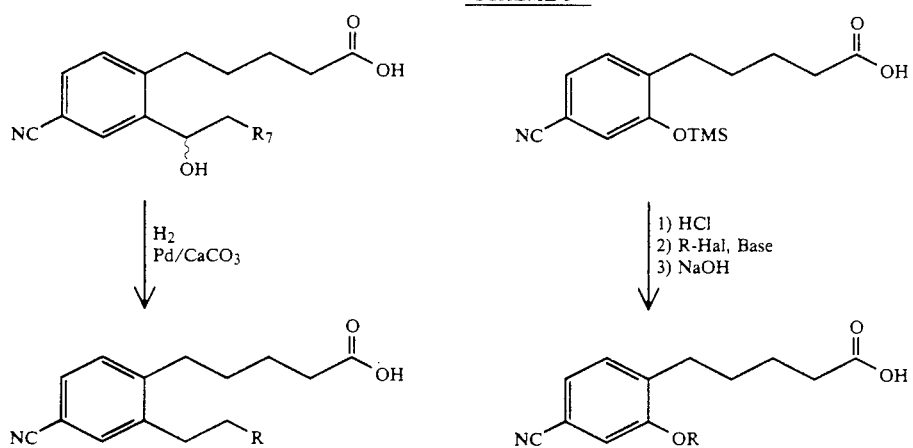
In the above scheme R is alkyl having 1 to 4 carbon atoms, $R_{10}$ is alkyl having 1 to 6 carbon atoms and $X_2$ is halo.
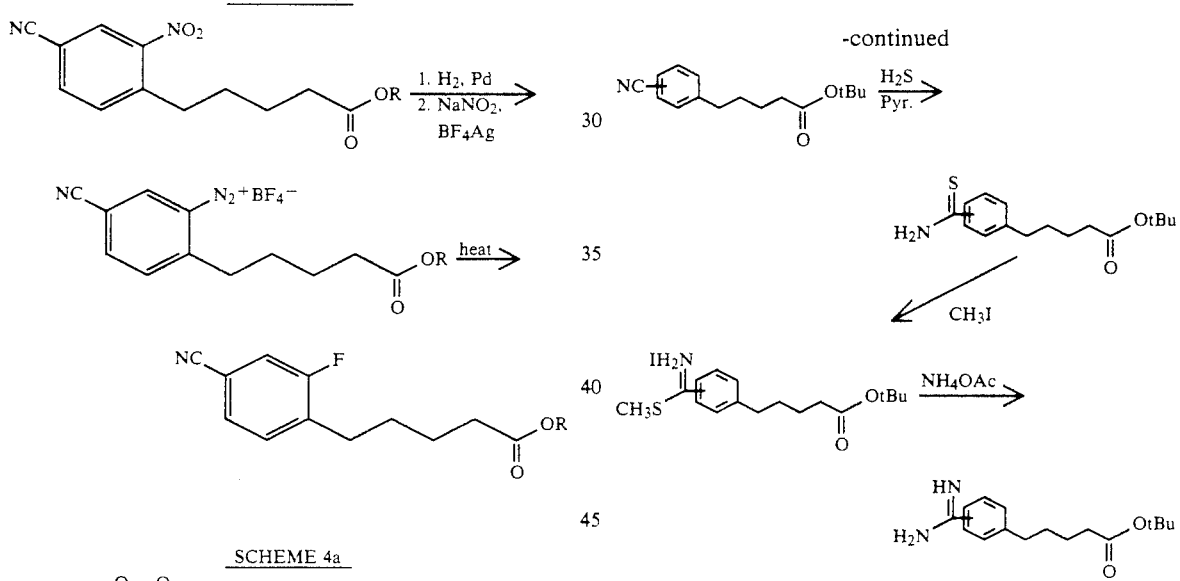
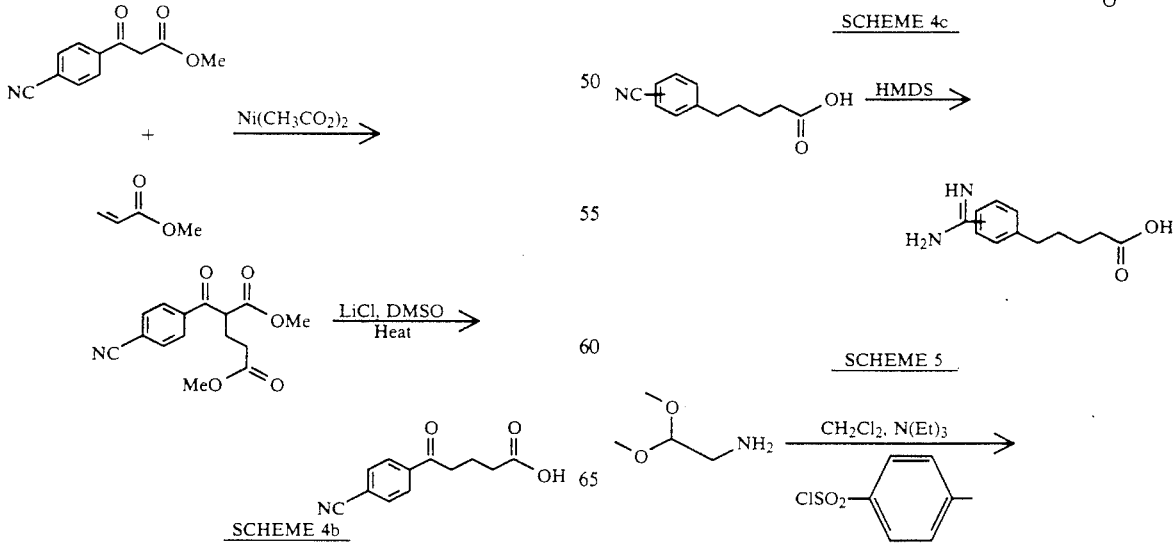
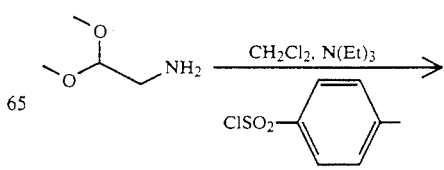

SCHEME 5 -continued
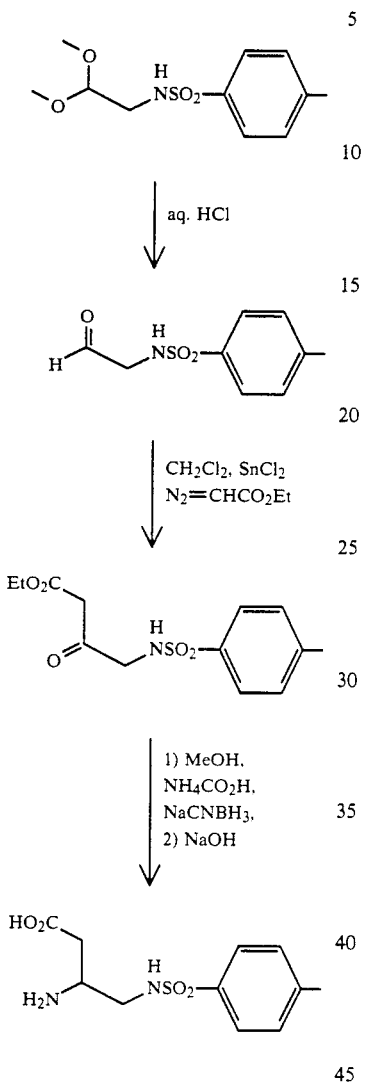
SCHEME 6 -continued
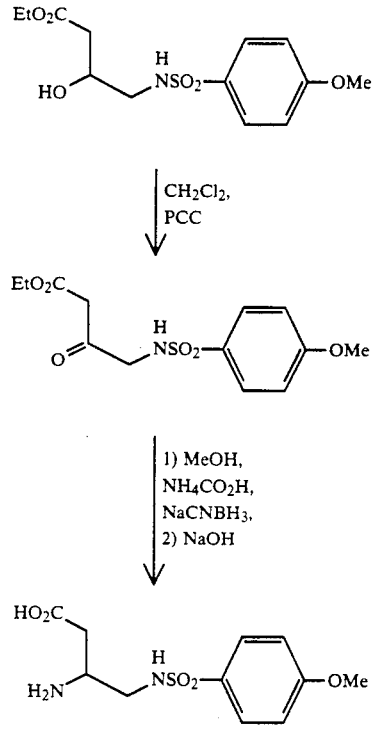
SCHEME 7
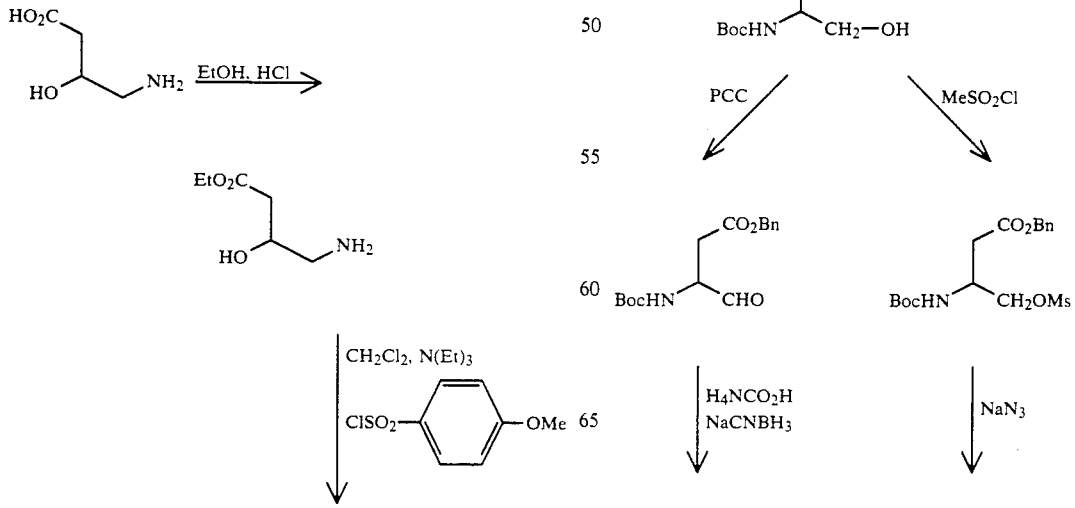

-continued
SCHEME 7

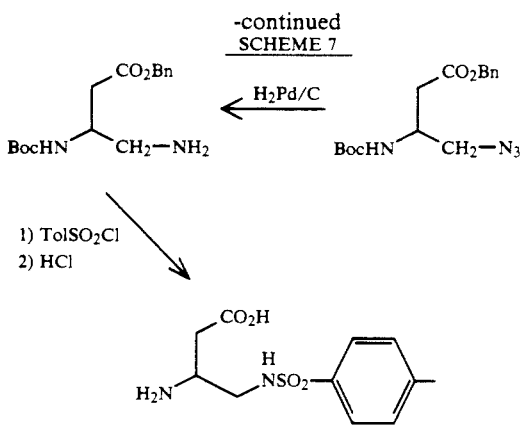

SCHEME 8

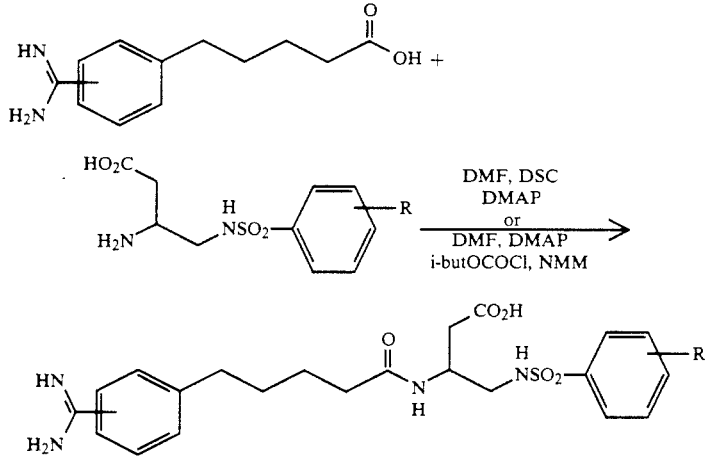

NMM = N-methylmorpholine; DMF = N,N-Dimethylformamide
DSC = N,N'-Disuccinimidyl carbonate
wherein R stands for substitution on the phenyl ring.

This invention also relates to a method of inhibiting platelet aggregation and more specifically, a method of treatment involving the administration of compounds of Formula I to achieve such inhibition.

For the inhibition of platelet aggregation, compounds of Formula I may be administered orally, parenterally, or by inhalation spray or rectally in dosage unit formulations containing conventional nontoxic pharmaceutically acceptable carriers, adjuvants and vehicles. The term parenteral as used herein includes, for example, subcutaneous, intravenous, intramuscular, intrasternal, infusion techniques or intraperitonally.

The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising one or more compounds of the present invention in association with one or more non-toxic, pharmaceutically acceptable carriers and/or diluents and/or adjuvants (collectively referred to herein as "carrier" materials) and if desired other active ingredients.

The dosage regimen for treating a condition with the compounds and/or compositions of this invention is based on a variety of factors, including the type, age, weight, sex and medical condition of the patient; the severity of the condition; the route of administration; and the particular compound employed. Thus dosage regimen may vary widely. Dosage levels of the order from about 0.01 mg to about 150 mg per kilogram of body weight per day are useful in the treatment of the above-indicated conditions (from about 10 mg to about 150 mg per patient per day). For oral administration a daily dose of from about 0.01 to 150 mg/Kg body weight, particularly from about 1 to 30 mg/Kg body weight may be appropriate. For administration by injection a preferred daily dose would be from about 0.01 to 50 mg/Kg body weight.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may contain, for example, an amount of active ingredient from about 1 to 250 mg, preferably from about 25 to 150 mg. A suitable daily dose for a mammal may vary widely depending on the condition of the patient and other factors.

The active ingredient may also be administered by injection as a composition wherein, for example, saline, dextrose or water may be used as a suitable carrier. A suitable daily dose would typically be about 0.01to 50 mg/kg body weight injected per day in multiple doses depending on the condition being treated.

For administration, the compounds of this invention are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the -pharmaceutical art.

The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

The following Examples are intended to further illustrate the present invention and not to limit the invention in spirit or scope. In the Examples, all parts are parts by weight and temperature is in degrees Celsius unless otherwise expressly set forth.

EXAMPLE 1

Preparation of
(±)-3-[[5-[4-Aminoiminomethyl)phenyl]-oxopentyl]amino]-4-[[(4-methylphenyl)sulfonyl]amino) Butanoic Acid

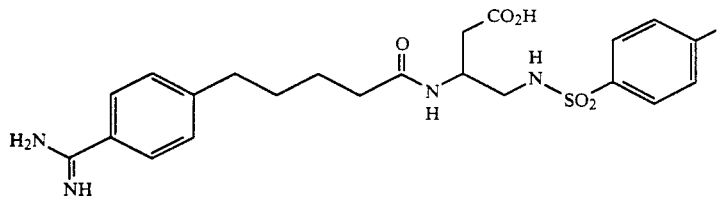

Step 1. Prepration of 3-Amino-4-[[(4- methylphenyl) sulfonyl]amino]butanoic Acid In a flask under nitrogen was added p-toluenelsulfonyl chloride (18.5 g, 95.2 mmol) to aminoacetaldehyde dimethyl acetal (10 g, 95.2 mmol), triethylamine (12.5 g, 114.2 mmol) and DMAP (100 mg) in methylene chloride at 0° C. The reaction was complete in 1h after which time water was added and the organic layer was separated. The organic layer was extracted with 1N HCl, dried over $Na_2SC_4$ and solvent was removed in vacuo. The dimethyl acetal was hydrolyzed by heating at 50°-60° C. in water/THF 1:1 containing 4 drops of concentrated HCl for 30 min. Following the removal of the solvent in vacuo, this intermediate aldehyde (20 g, 77.2 mmol) was immediately added to a mixture of ethyl diazoacetate (8.8 g, 77.2 mmol) and $SnCl_2$ (1.5 g, 0.7 mmol) stirring in methylene chloride at room temperature. After 2 hours the reaction mixture was washed with 1N HCl then dried over $Na_2SO_4$ and the solvent was removed in vacuo to afford 22 g of the β-ketoester. This material was dissolved in methanol (300 ml) containing ammonium formate (53 g, 0.85 mol), $NaCNBH_3$ (5.3 g, 85 mmol) was added and the reaction was allowed to stir for 24 h at room temperature. After completion of the reaction, the solvent was removed in vacuo affording an oily solid which was dissolved in ether and extracted into 6N HCl. The acid layer containing the β-amino ester was brought to pH 12 with 50% NaOH, and the resulting β-amino acid was isolated by on reverse phase chromatography. $^1$H NMR $d_6$ (DMSO) γ 2.4 (s, 3H), 2.6 (dd, 2H, $J_1=3.5$ HZ and $J_2-16$ Hz, 2.95 (bd, 2H, J=2.5 Hz), 3.49 (t, 1H, J=3.5 Hz), 7.4 (d, 2H, J=7.5 Hz), 7.7 (d, 2H, J=7.5 Hz); MS (FAB) m/e 273.1 (MH+).

Step 2. Preparation of
(±)-3-[[5-[4-(Aminoiminomethyl)phenyl]-1-oxopentyl]amino]-4-[[(4-methylphenyl)sulfonyl]amino]butanoic acid In a flask under nitrogen atmosphere, 5-(p-benzamidine)-pentanoic acid (1.5 g.) prepared in step 1, example 1 was added to dry DMF (20 ml) followed by the addition of N,N'-disuccinimidyl carbonate 1.5 g) and DMAP (100 mg) at 25° C. The mixture soon turned clear after which time the β-amino acid from step 1 (2 g) in aqueous $K_2CO_3$ was added. After 1 h the solvent was removed under reduced pressure and the product was purified by reverse phase chromatography (water-/acetonitrile) and lyophilized to give 1.6 g of a white solid: $^1$H NMR $d_6$(DMSO) γ 1.5 (m, 4H), 2.04 (t, 2H, J=7.5 Hz), 2.44 (s, 3H), 2.48 (dd, 2H,$J_1=3.8$ Hz, $J_2=17$ Hz), 2.68 (t, 2H, J=7.6 Hz), 2.5 (t, 2H, J=7.7 Hz), 4.02 (m, 1H), 7.55 (m, 9H), 9.5 (bs, 2H), 9.23 (bs, 2H); MS FAB) m/e 475.2 (MH+).

Elemental Analysis: Required for $C_{23}H_{30}N_4O_5S.F_3.C_2O_2H$:C 49.52;H 5.44;N 9.2;F 9.4. Found:C 49.42;H 5.17; N 9.14;F 9.22.

EXAMPLE 2

Preparation of
(±)-3-[[5-[4-(Aminoiminomethyl)phenyl]-1-oxopentyl]amino]-4-[[(4-methoxyphenyl)sulfonyl]amino]-butanoic Acid

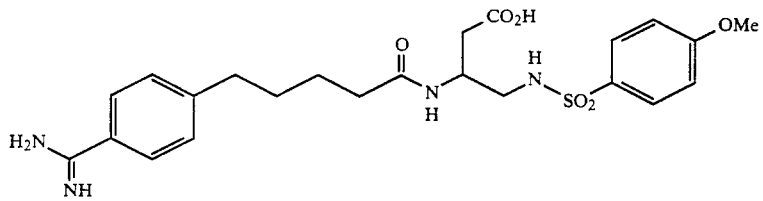

Step 3. Preparation of 3-amino-4[[(4-methoxyphenyl) sulfonyl]amino]butanoic Acid In a flask DL-γ-amino-β-hydroxybutyric acid (10 g, 84 mmol) was added to dry ethanol followed by 4N HCl in dioxane 20 ml). This mixture was heated to reflux for 4 h. The solvent was removed under reduced pressure to leave the ethyl ester hydrochloride. To a clear solution of ethyl DL-γ-amino-γ-hyroxybutyrate (12 g, 65.5 mmol) triethylamine (9.9 g, 98.3 mmol) in methylene chloride was added p-methoxybenzene sulfonyl chloride (15.5 g, 65.5 mmol) at 25° C. After complete reaction water was added and the layers separated. The organic material was washed with 1N HCl and dried over $Na_2SO_4$. The solvent was removed in vacuo to afford 24 g of ethyl γ-p-methoxy benzenesulfonamide-β-hydroxybutyrate. This solid was added to pyridinium chlorodichromate (PCC) (21 g, 98.3 mmol), solid $K_2CO_3$ (10 g) and molecular sieves (10 g) in methylene chloride at 25° C. The oxidation took place over a period of 5 h. The dark brown mixture was concentrated to 50 ml, then filtered through silica gel and eluted with ethyl acetate. Upon removal of the solvent the β-keto ester (10 g) was dissolved in methanol and $NH_4CO_2H$ (17 g, 272 mmol), $NaCNBH_3$ (1.7 g, 27 mmol) were added and allowed to stir for 24 h. The reductive amination was performed as above in step 1. The β-amino acid was purified by reverse phase chromatography (water/acetonitrile) to give 4 g of a white solid. $^1N$ NMR $d_6$ DMSO) γ 2.58 (s, 2H), 2.91 (t, 2H, J=8 Hz), 3.45 (m, 1H), 3.84 (s, 3H), 7.13 (d, 2H, J=7.5 Hz), 7.74 (d, 2H, J=7.5 Hz, 7.85 (t, 1H, J=6H z); MS (FAB) 289.08 (MN+).

Step 4. Preparation of (+-3-[[5-[4-(Aminoiminomethyl)phenyl]-1-oxopentyl]amino]-4-[[(4-methoxyphenyl)sulfonyl]amino]butanoic Acid In a flask under nitrogen atmosphere, 5-(p-benzamidine)-pentanoic acid (1.8 g.) prepared in step 1, example 1 was added to dry DMF (20 ml) followed by the addition of $N,N^1$-disuccinimidyl carbonate (1.8 g) and DMAP (100 mg) at 25° C. The mixture soon turned clear after which time the β-amino acid from step 3 (2 g) in aqueous $K_2CO_3$ was added. After 1 h the solvent was removed under reduced pressure and the product was purified by reverse phase chromatography (water/acetonitrile) and lyophilized to give 2.0 g of a white solid: $^1H$ NMR$_d6$(DMSO) γ 1.5 m, 4H), 2.04 (t, 2H, J=7.5 Hz), 2.38 (dd, 2H, $J_1$=3.8 Hz, $J_2$=17 Hz), 2.67 (t, 2H, J=7.6 Hz), 2.73 (t, 2H, J=7.7 Hz), 3 82 (3, 3H) 4.02 (m, 1H), 7.1 (d, 2H, J=7.2 Hz), 7.44 (d, 2H, J=7.3 Hz), 7.55 (t, 1H, J=8 Hz), 7.7 (d, 2H, J=8 Hz), 7.73 (d, 2H, J=Hz), 9.5 (bs, 2H), 9.23 (bs, 2H); MS (FAB) m/e (491.0 (MN+).

Elemental Analysis: Required for $C_{23}H_{30}N_4O_6S.F_3.C_2O_2H$:C 48.23;H 5.32;N 9.01; Found: C 47.82; H 4.95;N 8.94.

EXAMPLE 3

Preparation of (±) Ethyl-3-[[5-[5-(Aminoiminomethyl)phenyl]-1-oxopentyl]amino]-4-[[(4-methylphenyl)sulfonyl]amino]butanoate.

Step 5

In a flask (±)-3-[[5-[4-(Aminoiminomethyl)phenyl]-1-oxopentyl]amino]-4-[[(4-methylphenyl)sulfonyl]amino]butanoic acid (2.5 g) was placed followed by dry ethanol and 4N HCl in dioxane (10 ml). This mixture was allowed to stir for 2 h. After complete reaction the ethanol/dioxane was removed under reduced pressure and the product was purified by reverse phase chromatography (water/acetonitrile) and lyophilized to give 1.6 g of a white solid: $^1N$ NMR $d_6$(DMSO) γ1.12 (t, 3H, J=7.5 Hz), 1.5 (m, 4H), 2.04 (t, 2H, J=7.5 Hz), 2.44 (s, 3H), 2.45 (dd, 2H, $J_1$=3.8 Hz, $J_2$=17 Hz), 2.68 (t, 2H, J=7.6 Hz), 2.5 (t, 2H, J=7.7 Hz), 3.98 (q, 2H, J=7.5 Hz), 4.02 (m, 1H), 7.55 (m, 9H), 9.24 (bs, 4H); MS (FAB) m/e 503.3 (MN+).

Elemental Analysis: Required for $C_{25}H_{34}N_4O_5S.F_3.C_2O_2H$: C 51.11;H 5.84;N 8.88;F 8.98. Found:C 50.40; N 5.19; N 8.52; F 9.27.

EXAMPLE 4

Compounds of the invention were evaluated by an in vivo assay to determine compound activity as an inhibitors of platelet aggregation.

IN-VITRO PLATELET AGGREGATION IN PRP

Healthy male or female dogs were fasted for 8 hours prior to drawing blood; then 30 mL whole blood was collected using a butterfly needle and 30 cc plastic syringe with 3 ml of 0.129M buffered sodium citrate (3.8%). The syringe was rotated carefully as blood was drawn to mix the citrate. Platelet-rich plasma (PRP) was prepared by centrifugation at 975×g for 3.17 minutes at room temperature, allowing the centrifuge to coast to a stop without braking. The PRP was removed from the blood with a plastic pipette and placed in a plastic capped, 50 ml Corning conical sterile centrifuge tube which was held at room temperature. Platelet poor plasma (PPP) was prepared by centrifuging the remaining blood at 2000×g for 15 minutes at room temperature allowing the centrifuge to coast to a stop without braking. The PRP was adjusted with PPP to a count of 2-3×$10^8$s platelets per ml. 400 μL of the PRP preparation and 50 μL of the compound to be tested or saline were preincubated for 1 minute at 37° C. in a BioData aggregometer (BioData, Horsham, Pa.). 50 μL of adenosine 5'diphosphate (ADP) (50 μm final concentration) was added to the cuvettes and the aggregation was monitored for 1 minute. All compounds are tested in duplicate. Inhibition of aggregation for each sample was determined using the formula: % inhibition=($T_{inh}$--$T_{bas}$)/($T_{agg}$-$T_{bas}$×100 where $T_{bas}$ is % of light transmission in PRP (baseline), $T_{agg}$ is % of light transmission in the aggregated PRP sample (saline control) and $T_{inh}$ is % of light transmission in the sample containing the inhibitor.

The compounds tested, the inhibition observed at a test concentration of 10 μM, and the concentrations at

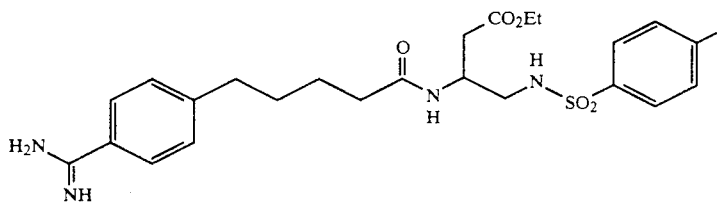

whcih the test compounds inhibit aggregation by 50% (IC$_{50}$) are recorded in Table 1.

TABLE I

| Compound | % Inhibition at 10 μM | Dog PRP IC$_{50}$ (μM) |
| --- | --- | --- |
| Example 1 | 100 | 1.0 |
| Example 2 | 100 | 8.0 |
| Example 3 | 20 | — |

What we claim is:

1. A compound of the formula

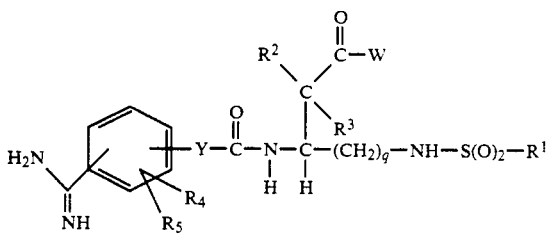

or a pharmaceutically acceptable salt thereof, wherein
$R^1$ is hydrogen, alkyl having 1 to 6 carbon atoms, phenyl or substituted phenyl wherein each substituent is selected from the group consisting of alkyl having 1 to 6 carbon atoms, halo, alkoxy having 1 to 6 carbon atoms, trifluoromethyl and hydroxy;
$R^2$ and $R^3$ are each independently hydrogen or alkyl having 1 to 6 carbon atoms;
$R^4$ and $R^5$ are each independently hydrogen, alkyl having 1 to 6 carbon atoms, alkoxy having 1 to 6 carbon atoms or halo;
W is the radical OR wherein R is hydrogen or alkyl having 1 to 6 carbon atoms;
Y is alkyl having 1 to 6 carbon atoms, alkenyl having 2 to 4 carbon atoms or alkynyl having 2 to 4 carbon atoms; and
q is an integer from 1 to 3.

2. A compound according to claim 1 of the formula

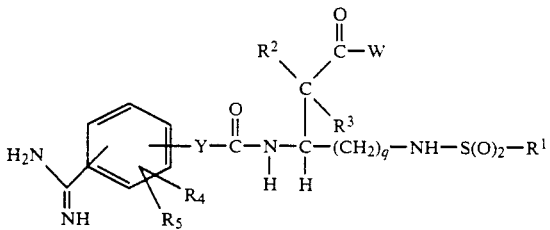

or a pharmaceutically acceptable salt thereof, wherein
$R^1$ is hydrogen, phenyl or substituted phenyl wherein each substituent is selected from the group consisting of alkyl having 1 to 6 carbon atoms, halo, alkoxy having 1 to 6 carbon atoms, trifluoromethyl and hydroxy;
$R^2$ and $R^3$ are each independently hydrogen;
$R^4$ and $R^5$ are each independently hydrogen;
W is the radical OR wherein R is hydrogen or alkyl having 1 to 6 carbon atoms;
Y is alkyl having 1 to 6 carbon atoms; and
q is an integer from 1 to 3.

3. A compound according to claim 2 wherein $R^1$ is phenyl.

4. A compound according to claim 2 wherein $R^1$ is substituted phenyl wherein each substituent can be selected from the group consisting of alkyl having 1 to 6 carbon atoms, halo, alkoxy having 1 to 6 carbon atoms, trifluoromethyl and hydroxy.

5. A compound according to claim 2 wherein W is the radical OR wherein R is hydrogen.

6. A compound according to claim 2 wherein W is the radical OR wherein R is alkyl having 1 to 6 carbon atoms.

7. A compound according to claim 5 wherein the compound is (±)-ethyl 3-[[5-[4-(aminoiminomethyl) phenyl]-1-oxopentyl]amino]-4-[[(4-methylphenyl) sulfonyl]amino]butanoate.

8. A compound according to claim 5 wherein the compound is (±)-3-[[5-[4-(aminoiminomethyl) phenyl]-1-oxopentyl]amino]-4-[[(4-methylphenyl) sulfonyl]amino]butanoic acid.

9. A compound according to claim 6 wherein the compound is (±)-3-[[5-[4-(aminoiminomethyl) phenyl]-1-oxopentyl]amino]-4-[[(4-methoxyphenyl) sulfonyl]amino]butanoic acid.

10. A pharmaceutical composition useful for inhibiting platelet aggregation comprising a therapeutically effective amount of a compound according to claim 1, together with one or more non-toxic pharmaceutically acceptable carriers.

11. A pharmaceutical composition according to claim 10 wherein the compound has the formula

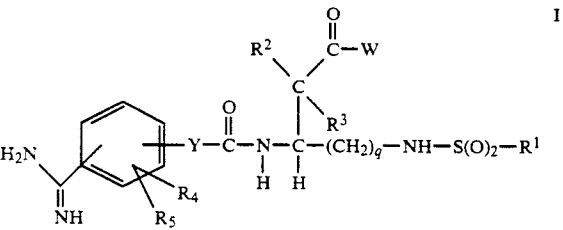

or a pharmaceutically acceptable salt thereof, wherein
$R^1$ is hydrogen, phenyl or substituted phenyl wherein each substituent is selected from the group consisting of alkyl having 1 to 6 carbon atoms, halo, alkoxy having 1 to 6 carbon atoms, trifluoromethyl and hydroxy;
$R^2$ and $R^3$ are each independently hydrogen;
$R^4$ and $R^5$ are each independently hydrogen;
W is the radical OR wherein R is hydrogen or alkyl having 1 to 6 carbon atoms;
Y is alkyl having 1 to 6 carbon atoms; and
q is an integer from 1 to 3.

12. A pharmaceutical composition according to claim 11 wherein the compound is (±)-ethyl 3-[[5-[4-(aminoiminomethyl)phenyl]-1-oxopentyl]amino]-4-[[(4-methylphenyl)sulfonyl]amino]butanoate.

13. A pharmaceutical composition according to claim 11 wherein the compound is (±)-3-[[5-[4-(aminoiminomethyl)phenyl]-1-oxopentyl]amino]-4-[[(4-methylphenyl) sulfonyl]amino]butanoic acid.

14. A pharmaceutical composition according to claim 11 wherein the compound is (±)-3-[[5-[4-[[(4-methoxyphenyl)sulfonyl]amino]butanoic acid.

15. A method of treating a mammal to inhibit platelet aggregation comprising administering a therapeutically effective dose of a compound according to claim 1 to a mammal in need of such treatment.

16. A method of treating a mammal to inhibit platelet aggregation according to claim 15 comprising administering a therapeutically effective dose of a compound of the formula

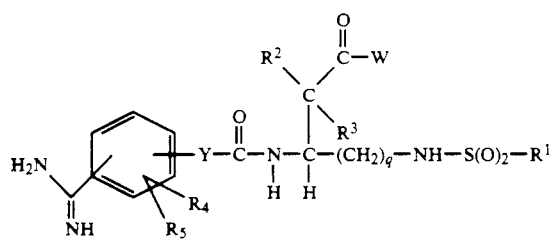

or a pharmaceutically acceptable salt thereof, wherein
$R^1$ is hydrogen, phenyl or substituted phenyl wherein each substituent is selected from the group consisting of alkyl having 1 to 6 carbon atoms, halo, alkoxy having 1 to 6 carbon atoms, trifluoromethyl and hydroxy;
$R^2$ and $R^3$ are each independently hydrogen;
$R^4$ and $R^5$ are each independently hydrogen;
W is the radical OR wherein R is hydrogen or alkyl having 1 to 6 carbon atoms;
Y is alkyl having 1 to 6 carbon atoms; and
q is an integer from 1 to 3.

17. A method according to claim 16 wherein the compound is (±)-ethyl 3-[[5-[4-(aminoiminomethyl)phenyl]-1-oxopentyl]amino]-4-[[(4-methylphenyl) sulfonyl]amino]butanoate.

18. A method according to claim 16 wherein the compound is (±)-3-[[5-[4-(aminoiminomethyl)phenyl]-1-oxopentyl]amino]-4-[[(4-methylphenyl)sulfonyl]amino]butanoic acid.

19. A method according to claim 16 wherein the compound is (±)-3-[[5-[4-(aminoiminomethyl)phenyl]-1-oxopentyl]amino]-4-[[(4-methoxyphenyl)sulfonyl]amino]butanoic acid.

* * * * *